Figure 1:
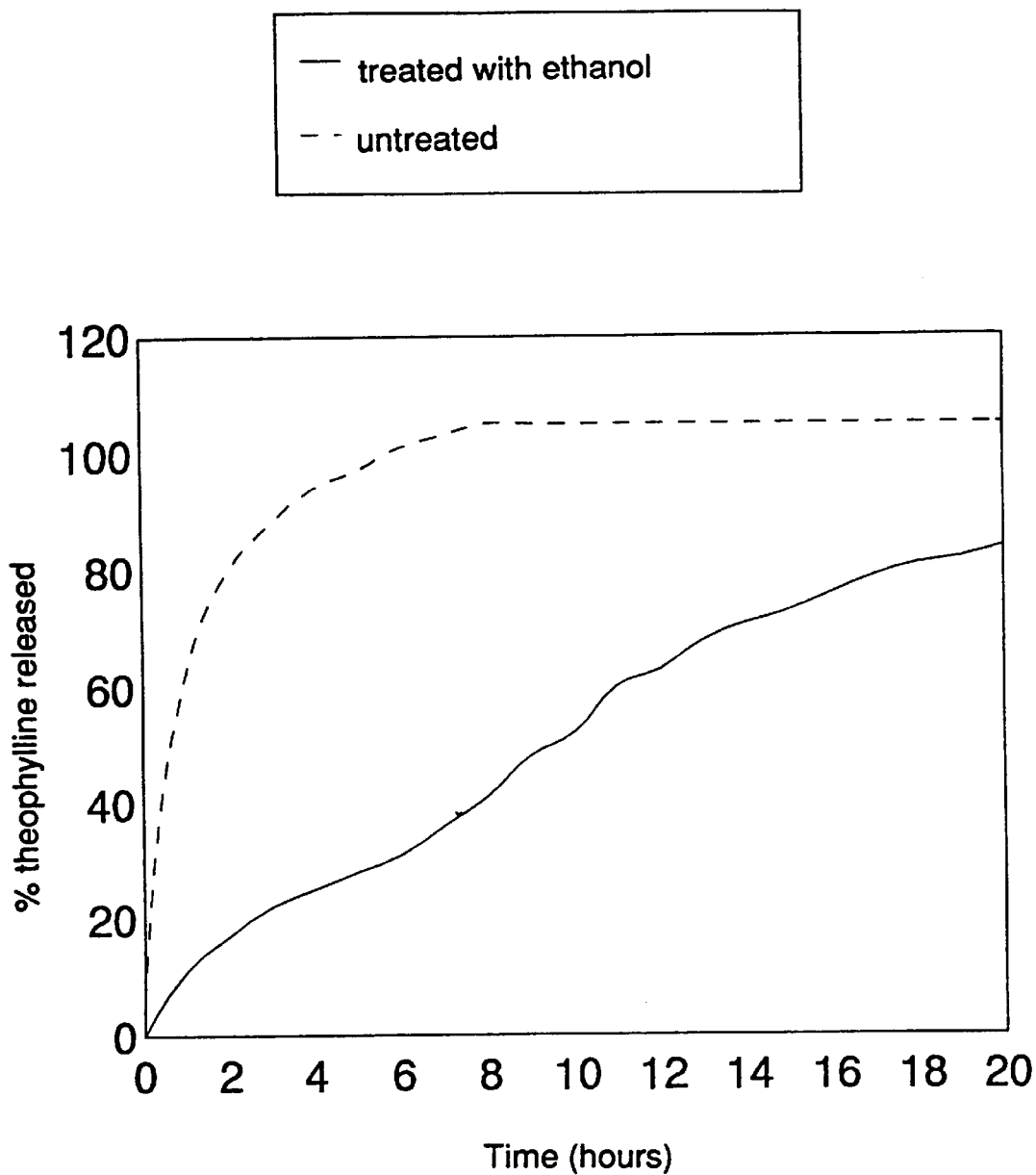

United States Patent [19]

Arends-Scholte et al.

[11] Patent Number: 6,010,717
[45] Date of Patent: Jan. 4, 2000

[54] STARCH PRODUCTS AS TABLETTING EXCIPIENT, METHOD FOR PREPARING SAME, AND METHOD FOR MAKING TABLETS

[76] Inventors: Anna Willemina Arends-Scholte, Kleine Brinkstraat 1c, Borger, Netherlands, 9531 JN; Jacob Bergsma, Hortuslaan 7, Haren, Netherlands, 9751 BE; Anko Cornelus Eissens, Marcus Buschstraat 62, Delfzijl, Netherlands, 9934 GM; Kornelis Fester Gottlieb, Wildervanckstraat 12, Veendam, Netherlands, 9643 LC; Coenraad Ferdinand Lerk, Braamlaan 8, Peize, Netherlands, 9321 GG; Josephus Johannes Swinkels, Kleine Vaartlaan 33, Veendam, Netherlands, 9642 PG; Gerrit Henk te Wierik, Boekenlaan 2, Groningen, Netherlands, 9731 LS

[21] Appl. No.: 08/809,904
[22] PCT Filed: Sep. 25, 1995
[86] PCT No.: PCT/NL95/00321
  § 371 Date: Mar. 24, 1997
  § 102(e) Date: Mar. 24, 1997
[87] PCT Pub. No.: WO96/09815
  PCT Pub. Date: Apr. 4, 1996
[30] Foreign Application Priority Data Sep. 27, 1994 [NL] Netherlands ............... 9401572

[51] Int. Cl.[7] ..................... A61K 9/20
[52] U.S. Cl. ............ 424/464; 424/489; 424/465
[58] Field of Search .................. 424/464, 489, 424/465, 499, 470; 106/210

[56] References Cited

U.S. PATENT DOCUMENTS 5,468,286  11/1995  Wai-Chiu et al. ............ 106/210

FOREIGN PATENT DOCUMENTS 0 449 648 A1  8/1992  European Pat. Off. .
1 554 703  10/1979  United Kingdom .
WO 94/01092  1/1994  WIPO .

OTHER PUBLICATIONS

Gerrit H.P. Te Wierik, Jacoba Van der Veen, Anko C. Eisens and Coenraad F. Lerk, Preparation, characterization and application of linear dextrins. Part VI. General applicability and mechanism of programmed release from amylodextrin tablets, *Journal of Controlled Release*, 27 (1993) 9–17.

Gerrit H.P. Te Wierik, Anko C. Eissens, Arie C. Besemer, and Conrad F. Lerk, Preparation, Characterization, and Pharmaceutical Application of Linear Dextrins. I. Preparation and Characterization of Amylodextrin, Metastable Amylodextrins, and Metastable Amylose, *Pharmaceutical Research*, vol. 10, No. 9, 1993.

Primary Examiner—Thurman K. Page
Assistant Examiner—William E. Benston, Jr.

[57] ABSTRACT

The invention relates to a tabletting excipient based on disintegrated starch granules, which is characterized by a content of long-chain amylose of at least 10% by weight based on the dry substance, a cold water-solubility of at most 25% by weight and a specific area of at least 1 $m^2/g$. The invention further relates to a method for preparing such tabletting excipient and to the use of the tabletting excipient in tablets.

13 Claims, 1 Drawing Sheet

STARCH PRODUCTS AS TABLETTING EXCIPIENT, METHOD FOR PREPARING SAME, AND METHOD FOR MAKING TABLETS

This application is a 371 of PCT/NL95/00321, filed Sep. 25, 1995.

This invention relates to specific starch products which are suitable as tabletting excipient, in particular as filler and/or binder. Tablets usually contain—in addition to the active ingredient such as a drug, vitamin, cleansing agent, color, insecticide or herbicide—particular inert components, often designated by the term of tabletting excipients. These tabletting excipients are classified according to their functional properties, such as binders, fillers, disintegrants, lubricants, flavors and colors. Suitable starch products can also fulfil several functions, such as the combination of binder and filler (often designated as filler/binder).

The starch products according to the invention are suitable in particular as filler/binder in tablets, pellets, pills, capsules and granules. For the manufacture of the tablets, the conventional production techniques can be used, viz. dry granulation, wet granulation and direct compression. The starch products according to the invention are suitable in particular in the manufacture of tablets by direct compression, whereby the powder mixture to be tabletted is introduced into the molds of a tabletting press and then compressed into tablets with a stamp.

Most kinds of starch consist of granules in which two types of glucose polymers occur, viz. amylose (15–35% by weight based on the dry substance) and amylopectin (65–85% by weight based on the dry substance). Amylose consists of substantially linear molecules with an average degree of polymerization (DP) of 1000–5000 (depending on the kind of starch). Amylopectin consists of very large, highly branched molecules with an average degree of polymerization of about 2,000,000. The commercially most important types of starch, viz. maize starch, potato starch, wheat starch and tapioca starch, contain 15–30% by weight of amylose. Of some types of cereal (barley, maize, millet, milo, rice and sorghum) and of potato starch, there exist varieties that consist substantially completely of amylopectin. These types of starch contain less than 5% by weight of amylose and are designated by the term amylopectin starches.

By debranching amylopectin molecules with so-called debranching enzymes, such as pullulanase and isoamylase, short-chain linear glucose polymers are obtained with a degree of polymerization which is substantially between 10 and 75. These products are designated as short-chain amylose, linear dextrin or amylodextrin, as opposed to long-chain amylose with a degree of polymerization of more than 100, which occurs naturally in starch granules or has been obtained by limited partial depolymerization of this amylose.

The use of various starch products as tabletting excipient is known. European patent specification 499 648 and International patent publication WO 94/01092 describe the use of low-molecular and/or high-molecular amylose products as tabletting excipient. The preparation and use of low-molecular or high-molecular amylose as tabletting excipient is also described in the following two journal articles:

G. H. P. Te Wierik, A. C. Eissens, A. C. Besemer and C. F. Lerk: Preparation, Characterization, and Pharmaceutical Application of Linear Dextrins: I. Preparation and Characterization of Amylodextrin, Metastable Amylodextrins, and Metastable Amylose. Pharmaceutical Research, Vol. 10, No. 9, 1993, pp. 1274–1279.

G. H. P. Te Wierik, A. C. Eissens, and C. F. Lerk: Preparation, Characterization and Pharmaceutical Application of Linear Dextrins: IV. Drug release from capsules and tablets containing amylodextrin. International Journal of Pharmaceutics 98 (1993) 219–224.

The starch products described in the above-mentioned publications have as disadvantages that they do not possess optimum tabletting properties, that the method of preparation is laborious and expensive and/or that relatively expensive and scarce amylopectin starches have to be used as starting material in the preparation. The starch products according to the invention possess excellent tabletting properties and are produced from amylose-containing types of starch.

The starch products that are used as tabletting excipient in accordance with the invention are characterized by:
- the absence of the original grain structure
- a content of long-chain amylose (DP at least 100) of at least 10% by weight based on the dry substance
- a cold water-solubility of at most 25%
- a specific area of at least 1 $m^2/g$.

The starch products according to the invention are produced from amylose-containing types of starch which contain at least 10% by weight (based on the dry substance) long-chain amylose. Suitable types of starch are potato starch, maize starch, tapioca starch, wheat starch, sago starch, and pea starch and high-amylose starch. Also eligible for use as starting material for the manufacture of the starch products according to the invention are modified amylose-containing starches which have been obtained by chemical, enzymatic and/or physical modification of the above-mentioned native amylose-containing types of starch.

Described hereinafter are preferred embodiments for the preparation of starch products according to the invention. The preparation of starch products is carried out in two steps, viz.:

1) The preparation of strongly hydrated (swollen) cold water-insoluble starch.

2) Dehydration of the resultant starch product by means of water-miscible organic solvents or by means of freeze-drying.

re 1) The Preparation of Hydrated Cold Water-Insoluble Starch.

In this preparation a distinction can be made between enzymatic methods (1A) and physical/chemical methods (1B).

1A) Enzymatic Methods

Here an aqueous solution of an amylose- and amylopectin-containing starch is treated with a debranching enzyme such as pullulanase or isoamylase. By the action of the debranching enzyme, amylopectin molecules are converted to low-molecular short-chain amylose. As debranching enzyme, for instance pullulanase (E.C. 3.2.41) from *Bacillus acidopullulyticus* can be used. Such an enzyme is sold under the name of Promozyme 200L by NOVO Nordisk A/S, Bagsvaerd, Denmark. The enzyme is supplied in standard form having an activity of 200 PUN/g and a density of 1.25 g/ml.

This debranching reaction is carried out in aqueous medium. The starch solution to be used can be prepared by heating an aqueous starch suspension above the gelatinizing temperature of the starch, for instance by means of a steam jet device (typically referred to as a jet cooker). The starch concentration to be used is preferably between 3 and 40% by weight.

The method is carried out at pH values between 3 and 9. The reaction temperature to be used is preferably between 40 and 65° C. Promozyme 200L is dosed in amounts between 0.1 and 10% by volume based on the dry substance. The reaction time is preferably between 2 hours and 24 hours. After this debranching reaction, the dextrose equivalent (DE) is preferably between 2 and 6. The debranching reaction is ended by adjusting the pH to 6–6.5.

Prior to, simultaneously with or subsequent to the debranching reaction, preferably a limited α-amylolysis is carried out with an α-amylase (EC 3.2.1.1), for instance from *Bacillus subtilis*. Such an enzyme is sold under the name of BAN 240L (Bacterial Amylase NOVO) by NOVO Nordisk A/S, Bagsvaerd, Denmark. The enzyme is supplied in standard form having an activity of 240 KNU/g and a density of 1.2 g/ml. This reaction is preferably carried out at a temperature of 50–60° C. An amount of 0.001–0.1% (v/w d.s.=vol./wt. dry substance) BAN 240L is dosed. The reaction time is preferably between 2 and 60 minutes. The reaction is stopped by lowering the pH to 2–2.5.

Under slow stirring, the reaction mixture is cooled for 10 to 24 hours to 15–20° C. The amylose flocks formed are isolated from the solution, for instance by filtration, centrifugation or separation. The isolated amylose product is then washed with water. The yield of amylose varies between 25 and 90% by weight expressed as a percentage of the starch originally used. The moisture content varies between 60 and 90% by weight. The dry substance fraction of the product consists of about 20–80% by weight of short-chain amylose (DP of 10–75) and 80–20% by weight of long-chain amylose (DP above 100).

1B) Physical/Chemical Methods

British patent specification 1,554,703 discloses a method for making cold water-insoluble starch products by suspending cold water-soluble starches in aqueous solutions of salts which can effectively raise the swelling temperature. By maintaining the products in contact with this salt solution, the starches become cold water-insoluble. Salts such as magnesium sulfate, ammonium sulfate, ammonium phosphate and sodium sulfate are effective. Pregelatinized, cold water-soluble starches, for instance roller-dried starch (Paselli-WA4) can serve as starting material.

The method is carried out in aqueous salt solutions. The pregelatinized starch products (3–25% by weight of moisture) are suspended in salt solutions, which preferably contain 30–45 parts by weight of the above-mentioned salts. The suspension is stirred for 15 minutes to 50 hours at 15–25° C. Then the resultant cold water-insoluble starch product is isolated from the solution, for instance by filtration, centrifugation or separation. The hydrated product is washed free of salt with water.

re 2) Dehydration by Means of Water-Miscible Organic Solvents or by Freeze-Drying.

The products mentioned under 1) are strongly swollen and the dry substance content in the products obtained by filtration, centrifugation or separation is low (10–40% by weight). In order to be able to process the products into tablet formulations, the dry substance content has to be raised to 85–95% by weight.

The manner of dehydration influences the tabletting properties of the hydrated starch products.

A considerable increase of the breaking strength of the tablets is realized by dehydrating the starch products with water-miscible organic solvents such as ethanol, isopropanol, n-propanol, methanol or acetone. By this treatment, products are obtained which, upon compression to tablets, exhibit a strong dry bond, to the extent that the binding force of microcrystalline cellulose can be surpassed.

Another method for dehydrating the swollen starch products is freeze-drying. By this drying technique, too, starch products are obtained with better tabletting properties than when other drying techniques are used, such as air drying, vacuum drying, spray drying or pneumatic drying.

By the use of the above-described methods, starch products are obtained which have completely lost the original granular structure. Owing to the starting material being amylose-containing starches, the produced hydrated starch products still contain at least 10% by weight of long-chain amylose (DP of at least 100) and preferably at least 15% by weight based on the dry substance. The cold water-solubility of the starch products according to the invention (as hereinafter described) is not more than 25%, preferably not more than 15% and most preferably not more than 10%.

The specific area (BET) of the starch products according to the invention (as hereinafter described) is above 1 $m^2/g$, preferably above 3 $m^2/g$ and most preferably above 6 $m^2/g$.

To prevent friction between the tabletting powder and the tabletting machine during the preparation of tablets, often magnesium stearate is added as a lubricant. However, magnesium stearate has a negative influence on the binding properties of most binders, including microcrystalline cellulose. It has been found that the starch products according to the invention, which largely consist of amylose (short-chain and long-chain), show little or no deterioration in the binding properties as a result of the presence of magnesium stearate. These starch products accordingly possess minor magnesium stearate sensitivity.

It has further been found that the starch products according to the invention, which largely consist of amylose (short-chain and long-chain), are eminently suitable tabletting excipients for the manufacture of tablets with programmed release systems (controlled release). These systems are to reduce any side effects of drugs and to realize a low dosage by releasing the drug with a delay, gradually or at a constant rate. A constant release of the drug is often more favorable because then a constant concentration of the active substance prevails in the blood over a longer time. Ideally, the tablet affords a constant rate of release of the drug. This is sometimes referred to as a zero-order profile. Controlled-release tablets are normally struck at relatively high compression forces, so that they possess minor porosity.

The invention is further explained in and by the following examples. In the text, the examples and the claims, a number of terms and assay methods are mentioned, which are described in more detail hereinafter.

Moisture Content

The moisture content of the powders was determined by drying 5 g product to a constant weight on a moisture balance at 105° C. The moisture content is determined from the loss of weight.

Bulk Density

The bulk density of the powders (ml/g) was determined by charging a particular amount of product (about 25 g) to a graduated measuring cylinder of a volume of 50 ml and a diameter of 2.2 cm. The bulk density is determined from the bulk volume.

Swollen Volume 5 g powder was charged to a graduated measuring cylinder of a volume of 100 ml. After addition of 80 ml demineralized water of 25° C., the suspension is mixed to remove air bubbles. The volume is supplemented to 100 ml with demineralized water. The measuring cylinder is closed and the suspension is left for 24 hours. The volume of the swollen product is determined. The swollen volume is expressed in millilitres per gram of dry substance.

Cold Water-Soluble Fraction

An amount of powder corresponding with 3 g dry substance is suspended in 297 ml distilled water at 25° C. The suspension is stirred for 2 minutes at 1500 rpm. The suspension is centrifuged for 15 minutes at 2000 rpm. An amount of 30 ml of the supernatant is evaporated on a steam bath. Then the residue is dried to a constant weight at 110° C. The weight of the residue is multiplied by 1000 and divided by the original amount of dry weight. The resultant value is the cold water-soluble fraction. The assay is carried out in triplicate and the values are averaged.

Specific Area (BET)

The specific area (BET) was determined by means of nitrogen adsorption with a Quantasorp gas adsorption appliance (Quantachrome Corp., Syosset U.S.A.).

Porosity

The porosity of tablets was calculated from the tablet dimensions, the tablet weight and the real density of the powders determined with a (He)-pycnometer, model HVP-1 (Quantachrome Corp., Syosset U.S.A.). The porosities were determined in triplicate.

Controlled Release Experiments

Controlled release experiments with tablets were carried out in a paddle appliance (Prolab, Rhône-Poulenc, Paris, France) under conditions as specified in the USP XXI. The medium (1000 ml 50 mM phosphate buffer, pH 6.8) was deaerated. The experiments are carried out at 37° C. The stirring speed is 100 rpm. The concentrations of the pharmacon were determined by spectrophotometry using an Ultrospec 4052 TDS appliance (LKB, Zoetermeer) at 268 nm. The experiments were carried out in triplicate. (BE/SW 51).

EXAMPLE 1

An aqueous starch suspension with a potato starch concentration of 20% by weight was gelatinized in a jet cooker by heating at 150° C. After adjustment of the pH to 5.2 the mixture was cooled to 58° C. Then Promozyme 200L was added in a dosage of 1% by volume per gram of dry substance. After reaction for 4 hours the DE was 2.4.

After lowering of the temperature to 46° C. and adjustment of the pH to 6.0, 0.007% (v/w d.s.) BAN 240L was dosed. After 20 minutes the reaction was stopped by lowering the pH to 2.3.

Under slow stirring the reaction mixture was cooled to 17° C. in 16 hours. The resultant amylose flocks were separated from the solution by means of vacuum filtration over cloth.

The product was resuspended in water and filtered again. This procedure was repeated until the amount of material that could be washed out in the washing liquid was less than 1% by weight.

The filtered product (Amylose BF) had a dry substance content of 20% by weight.

The dry substance fraction of the product contains 65% by weight of long-chain amylose and 35% by weight of short-chain amylose.

Portions of the product were either dried directly or first treated with water-miscible organic solvents and then dried. Table 1 lists some properties of the resultant dried starch products. The product Avicel PH 101 is a type of microcrystalline cellulose which is used as filler/binder in tablets.

TABLE 1

Powder properties of Amylose BF products after different dehydration and drying methods Product designation:
BF(1) air dried
BF(2) spray dried TABLE 1-continued Powder properties of Amylose BF products after different dehydration and drying methods BF(3) pneumatically dried
BF(4) product washed thrice with a 40-fold (v/w) excess of 96% ethanol and then dried in air.
BF(5) product freeze-dried.

| Designation | Moisture content (wt. %) | Bulk density (g/ml) | Swollen volume (ml/g d.s.) | Cold water solubility (wt. %) | Specific area (BET) (m$^2$/g) |
|---|---|---|---|---|---|
| BF(1) | 11.3 | 0.67 | 4.9 | 1.8 | 0.43 |
| BF(2) | 9.8 | 0.66 | 4.4 | 5.5 | 0.10 |
| BF(3) | 11.3 | 0.67 | 4.3 | 5.6 | 0.39 |
| BF(4) | 13.3 | 0.68 | 5.9 | 8.4 | 7.0 |
| BF(5) | 9.8 | 0.67 | 6.0 | 9.1 | 23.0 |
| Avicel PH 101 | 5.8 | 0.65 | 4.5 | 0 | 0.93 |

From the products listed in Table 1, tablets were produced by means of direct compression (See Table 2). The breaking strengths in the presence and absence of the lubricant magnesium stearate were determined. Striking is the observation that the compression force necessary for manufacturing hard tablets based on air-dried and spray-dried products has to be large (15 kN). Considerably higher breaking strengths are realized on the basis of products obtained by treatment with water-miscible organic solvents or by freeze-drying. These high breaking strengths are obtained at a relatively low compression force (3 kN). It further appears that the last-mentioned products are not sensitive to magnesium stearate under the specified conditions.

TABLE 2

Breaking strengths and magnesium stearate sensitivity of Amylose BF products after different dehydration and drying methods.

For the description of the products, see the legend to Table 1.
From the products, tablets were struck at the specified compression force. The breaking strength (BVH) was determined for tablets of 300 mg and a diameter of 13 mm, manufactured at the specified compression force. The breaking strength in the presence of magnesium stearate (BVH Mg st.) was determined after mixing of the product with 0.5% (w/w) magnesium stearate for two minutes. The lubricant sensitivity is expressed in the lubricant sensitivity ratio (LSR). This is the ratio between the reduction of the breaking strength of tablets as a result of the presence of magnesium stearate and the breaking strength of unlubricated tablets.

| Production method | Method of treatment | Compression force (kN) | BVH (N) | BVH (Mg st.) (N) | LSR |
|---|---|---|---|---|---|
| BF(1) | Air drying | 15 | 181 | 35 | +0.81 |
| BF(2) | Spray drying | 2 | >30 | 14 | >+0.53 |
| BF(3) | Pneumatic drying | 3 | 55 | n.d.*) | n.d.*) |
| BF(4) | Ethanol + air | 3 | 170 | 182 | −0.07 |
| BF(5) | Freeze-drying | 3 | 207 | 189 | +0.09 |
| Avicel PH 101 | | 3 | 83 | 60 | +0.28 |

*) n.d.: not determinable

EXAMPLE 2

Cold water-insoluble Paselli WA4 was obtained by means of magnesium sulfate precipitation of Paselli WA4, as follows.

In 500 ml salt solution, containing 30 parts $MgSO_4.7 H_2O$ in 98 parts demineralized water, 75 g Paselli WA4 was suspended under stirring. After stirring for 5 hours, the swollen product was separated by means of filtration. The product was washed by resuspending the filter cake in demineralized water and subsequent filtration. This method was repeated until the product was free of salt. The filtered product (cold water-insoluble Paselli WA4) had a dry substance content of 20% by weight.

The cold water-insoluble starch product was washed thrice with a 40-fold (v/w) excess of 96% ethanol and once with a 40-fold excess of absolute ethanol. After drying in the air, the moisture content was 10.7% by weight. The bulk density was 0.35 g/ml. The swollen volume was 5.9 ml/g d.s. The dry substance fraction of the product contains 20% by weight of long-chain amylose. The cold water-solubility of the product was 2% by weight. The specific area (BET) is 10.2 $m^2/g$. The breaking strength of tablets (300 mg, diameter 13 mm) manufactured by means of direct compression (3 kN) was 91 N.

EXAMPLE 3

Amylose BF was mixed with different amounts of 96% ethanol (See Table 3). The treated products were separated by means of filtration and the products were dried in air. After drying, the products were conditioned to the equilibrium moisture content.

The properties of the thus obtained products are summarized in Table 3. From this table it appears that the specific area increases upon increase of the ethanol:water ration (present in the Amylose BF flock). The breaking strength increases upon enlargement of the specific area.

TABLE 3

Properties of Amylose BF after treatment with different amounts of 96% ethanol.

| Number ml ethanol per 50 g Amylose BF | BET ($m^2/g$) | Moisture content (%) | BVH at 3 kN (N) | Porosity at 3 kN | Bulk density (g/ml) |
|---|---|---|---|---|---|
| 0 | 0.43 | 13.6 | 47 | 0.40 | 0.66 |
| 5 | 0.62 | 12.7 | 44 | 0.37 | 0.66 |
| 10 | 0.42 | 12.6 | 45 | 0.38 | 0.67 |
| 20 | 0.44 | 14.5 | 59 | 0.36 | 0.67 |
| 25 | 0.50 | 19.2 | 77 | 0.30 | 0.67 |
| 50 | 0.88 | 16.9 | 94 | 0.35 | 0.67 |
| 100 | 1.22 | 15.4 | 84 | 0.40 | 0.67 |
| 200 | 2.06 | 15.0 | 92 | 0.40 | 0.66 |
| 500 | 3.12 | 15.1 | 103 | 0.41 | 0.67 |
| Avicel PH 101 | 0.93 | 5.9 | 83 | | 0.65 |

EXAMPLE 4

In this example, Amylose BF (See Example 1) is used as tabletting excipient in tablets with controlled release.

Amylose BF treated with ethanol [BF(4) of Example 1] (70% by weight) was mixed with theophylline (30% by weight) in a Turbula mixer for 30 minutes. This physical mixture was then mixed for 30 minutes with 0.5% by weight of magnesium stearate in a Turbula mixer.

From these mixtures, tablets were struck at 15 kN. The release profile is shown in FIG. 1. The pharmacon is released with a zero-order kinetics. The presence of magnesium stearate has no significant influence on the release profile.

Tablets manufactured with Amylose BF which has not been treated with ethanol [BF(1) of Example 1] disintegrate (FIG. 1). These products are therefore not suitable for the application.

We claim:

1. A tabletting excipient comprising a starch powder prepared from starch granules, said starch powder comprising a long-chain amylose content of at least about 10% by weight based on dry substance, a specific area of at least about 1 $m^2/g$, and a cold water-solubility of at most about 25% by weight.

2. A tabletting excipient according to claim 1, wherein said long-chain amylose content is at least about 15% by weight.

3. A tabletting excipient according to claim 2, wherein said starch powder has a cold water solubility of at most about 15% by weight.

4. A tabletting excipient according to claim 2, wherein said starch powder has a cold water solubility of at most about 10% by weight.

5. A tabletting excipient according to claim 2, wherein said starch powder has a specific area of at least about 3 $m^2/g$.

6. A tabletting excipient according to claim 2, wherein said starch powder has a specific area of at least about 6 $m^2/g$.

7. A tabletting excipient according to claim 2, wherein said starch powder further comprising a short-chain amylose.

8. A tabletting excipient according to claim 7, wherein said short-chain amylose has a content of about 20 to about 80% by weight based on dry substance, and wherein said long-chain amylose has a content of about 20 to about 80% by weight based on dry substance.

9. A method for preparing a tabletting excipient which comprises:
   (a) treating an aqueous solution comprising gelatinized starch with (1) a debranching enzyme or (2) a debranching enzyme and α-amylase to form a hydrated starch product which comprises short-chain amylose in addition to long-chain amylose,
   wherein said gelatinized starch comprising amylose and amylopectin, and
   wherein said long chain amylose content being at least about 10% by weight based on dry substance; and
   (b) dehydrating said hydrated starch product by (1) freeze drying said hydrated starch product or (2) treating said hydrated starch product with water miscible organic solvent and subsequently drying the thus treated starch product to produce the tabletting excipient as a starch powder, said starch powder having a specific area of at least about 1 $m^2/g$ and a cold water-solubility of at most about 25% by weight.

10. A method for preparing a tabletting excipient which comprises:
   (a) treating an aqueous solution said gelatinized starch with (1) a debranching enzyme or (2) a debranching enzyme and α-amylase to form a hydrated starch product which comprises short-chain amylose in addition to long-chain amylose,
   wherein said gelatinized starch comprising amylose and amylopectin,
   wherein said short-chain amylose content being about 20 to about 80% by weight based on dry substance, and wherein, said long-chain amylose content being about 20 to about 80% by weight based on dry substance; and (b) dehydrating said hydrated starch product by (1) freeze drying said hydrated starch or (2) treating said hydrated starch product with a miscible organic solvent and subsequently drying the thus treated starch product to produce the tabletting excipient as a starch powder, said starch powder having a specific area of at least about 1 $m^2/g$ and a cold water-solubility of at most about 25% by weight.

11. A method for preparing a tablet which comprises directly compressing a tabletting mixture with a filler or binder, wherein said filter or binder is a tabletting excipient comprising a starch powder prepared from starch granules, said starch powder having a long-chain amylose content of at least about 10% by weight based on the dry substance, a specific area of at least about 1 $m^2/g$, and a cold water-solubility of at most about 25% by weight.

12. A method for preparing a controlled-release tablet which comprises mixing a tabletting mixture with a tabletting excipient comprising a starch powder prepared from starch granules, wherein said starch powder comprising short chain amylose in addition to long-chain amylose, and wherein said long-chain amylose content is at least about 10% by weight based on dry substance, and having a specific area of at least about 1 $m^2/g$ and a cold water-solubility of at most about 25% by weight.

13. A method for preparing a controlled-release tablet which comprises mixing a tabletting mixture with a tabletting excipient comprising a starch powder prepared from starch granules, wherein said starch powder comprising short-chain amylose in addition to long-chain amylose, and wherein said short-chain amylose content is about 20 to about 80% by weight based on dry substance and the long-chain amylose content is about 20 to about 80% by weight based on dry substance, and having a specific area of at least about 1 $m^2/g$ and a cold water-solubility of at most about 25% by weight.

* * * * *